(12) United States Patent
Ketcham et al.

(10) Patent No.: US 9,631,222 B2
(45) Date of Patent: Apr. 25, 2017

(54) FILTER AND BLOWER GEOMETRY FOR PARTICLE SAMPLER

(71) Applicant: Particle Measuring Systems, Inc., Boulder, CO (US)

(72) Inventors: Cliff Ketcham, Golden, CO (US); Paul B. Hartigan, Longmont, CO (US); Ronald W. Adkins, Erie, CO (US)

(73) Assignee: Particle Measuring Systems, Inc., Boulder, CO (US)

( * ) Notice: Subject to any disclaimer, the term of this patent is extended or adjusted under 35 U.S.C. 154(b) by 0 days.

(21) Appl. No.: 14/645,857

(22) Filed: Mar. 12, 2015

(65) Prior Publication Data

US 2016/0002700 A1    Jan. 7, 2016

Related U.S. Application Data

(60) Provisional application No. 61/953,101, filed on Mar. 14, 2014.

(51) Int. Cl.
*C12Q 1/24* (2006.01)
*G01N 1/22* (2006.01)
(Continued)

(52) U.S. Cl.
CPC ............... *C12Q 1/24* (2013.01); *G01N 1/14* (2013.01); *G01N 1/2205* (2013.01);
(Continued)

(58) Field of Classification Search
CPC .... G01N 1/2202; G01N 1/24; G01N 15/0606; G01N 15/1434; G01N 1/14;
(Continued)

(56) References Cited

U.S. PATENT DOCUMENTS 4,231,133 A    11/1980  Probost
4,560,395 A    12/1985  Davis
(Continued)

FOREIGN PATENT DOCUMENTS

WO    WO 94/15153       7/1994
WO    WO 2008/027970    3/2008

OTHER PUBLICATIONS

Biswas et al. (1984) "High-velocity inertial impactors," Environ. Sci. Technol. 18(8):611-616.
(Continued)

*Primary Examiner* — Sally Merkling
(74) *Attorney, Agent, or Firm* — Lathrop & Gage LLP

(57) ABSTRACT

The invention provides devices and methods for sampling, detecting and/or characterizing particles. Devices and methods of the invention, including particle samplers, impactors and counters, include a filter component for removing particles in the exhaust flow of the device, for example, to eliminate or minimize the potential for the device itself to provide source of particles in an environment undergoing particle monitoring. This aspect of the present devices and methods is particularly useful for monitoring particles in manufacturing environments requiring low levels of particles, such as cleanroom environments for electronics manufacturing and aseptic environments for manufacturing pharmaceutical and biological products.

26 Claims, 7 Drawing Sheets

Figure 1A:
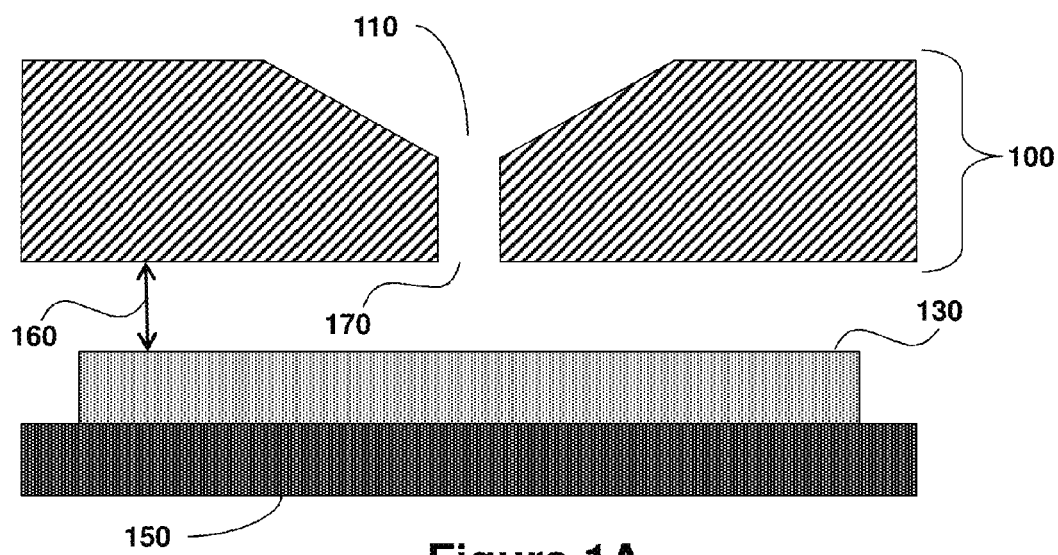

(51) Int. Cl.
*G01N 1/14* (2006.01)
*G01N 15/14* (2006.01)
*G01N 15/06* (2006.01)
*G01N 1/24* (2006.01)

(52) U.S. Cl.
CPC ......... *G01N 1/2208* (2013.01); *G01N 1/2273* (2013.01); *G01N 15/1434* (2013.01); *G01N 15/0606* (2013.01); *G01N 2001/2223* (2013.01); *G01N 2001/245* (2013.01)

(58) Field of Classification Search
CPC .. G01N 1/2205; G01N 1/2208; G01N 1/2273; G01N 2001/2223; G01N 2001/245; A47L 5/22; A47L 9/22; C12Q 1/24
See application file for complete search history.

(56) References Cited

U.S. PATENT DOCUMENTS

| | | | |
|---|---|---|---|
| 4,594,715 A | 6/1986 | Knollenberg | |
| 4,629,482 A | 12/1986 | Davis | |
| 4,798,465 A | 1/1989 | Knollenberg | |
| 4,893,928 A | 1/1990 | Knollenberg | |
| 5,032,721 A | 7/1991 | Bacon et al. | |
| 5,095,206 A | 3/1992 | Bacon, Jr. et al. | |
| 5,234,838 A | 8/1993 | Bacon, Jr. | |
| 5,282,151 A | 1/1994 | Knollenberg | |
| 5,283,199 A | 2/1994 | Bacon, Jr. et al. | |
| 5,330,722 A | 7/1994 | Pick et al. | |
| 5,358,443 A | 10/1994 | Mitchell et al. | |
| 5,512,086 A | 4/1996 | Glucksman | |
| 5,515,164 A * | 5/1996 | Kreikebaum | G01N 1/2273 250/576 |
| 5,671,046 A | 9/1997 | Knowlton | |
| 5,726,753 A | 3/1998 | Sandberg | |
| 5,751,422 A | 5/1998 | Mitchell | |
| 5,753,000 A | 5/1998 | Chiu et al. | |
| 5,753,002 A | 5/1998 | Glucksman | |
| 5,805,281 A | 9/1998 | Knowlton et al. | |
| 5,861,950 A | 1/1999 | Knowlton | |
| 5,889,589 A | 3/1999 | Sandberg | |
| 5,903,338 A | 5/1999 | Mavliev et al. | |
| 5,904,744 A | 5/1999 | Kagan | |
| 6,099,608 A | 8/2000 | Harms et al. | |
| 6,167,107 A | 12/2000 | Bates | |
| 6,246,474 B1 | 6/2001 | Cerni et al. | |
| 6,275,290 B1 | 8/2001 | Cerni et al. | |
| 6,481,050 B1 * | 11/2002 | Wilson | A47L 9/22 15/413 |
| 6,615,679 B1 | 9/2003 | Knollenberg et al. | |
| 6,709,311 B2 | 3/2004 | Cerni | |
| 6,859,277 B2 | 2/2005 | Wagner et al. | |
| 6,903,818 B2 | 6/2005 | Cerni et al. | |
| 6,945,090 B2 | 9/2005 | Rodier | |
| 7,030,980 B1 | 4/2006 | Sehler et al. | |
| 7,088,446 B2 | 8/2006 | Cerni | |
| 7,088,447 B1 | 8/2006 | Bates et al. | |
| 7,208,123 B2 | 4/2007 | Knollenberg et al. | |
| 7,235,214 B2 | 6/2007 | Rodier et al. | |
| RE39,783 E | 8/2007 | Cerni et al. | |
| 7,456,960 B2 | 11/2008 | Cerni et al. | |
| 7,576,857 B2 | 8/2009 | Wagner | |
| 7,667,839 B2 | 2/2010 | Bates | |
| 7,796,255 B2 | 9/2010 | Miller | |
| 7,916,293 B2 | 3/2011 | Mitchell et al. | |
| 7,973,929 B2 | 7/2011 | Bates | |
| 7,985,949 B2 | 7/2011 | Rodier | |
| 8,027,035 B2 | 9/2011 | Mitchell et al. | |
| 8,154,724 B2 | 4/2012 | Mitchell et al. | |
| 8,167,591 B1 | 5/2012 | Sorensen | |
| 8,174,697 B2 | 5/2012 | Mitchell et al. | |
| 8,427,642 B2 | 4/2013 | Mitchell et al. | |
| 8,800,383 B2 | 8/2014 | Bates | |
| 2005/0028593 A1 | 2/2005 | Rodier | |
| 2008/0087108 A1 * | 4/2008 | Kreikebaum | G01N 1/2202 73/863.23 |
| 2009/0078862 A1 | 3/2009 | Rodier et al. | |
| 2009/0190128 A1 | 7/2009 | Cerni et al. | |
| 2009/0268202 A1 | 10/2009 | Wagner | |
| 2013/0025454 A1 | 1/2013 | Moredock et al. | |
| 2013/0091656 A1 | 4/2013 | Smith | |
| 2013/0091810 A1 | 4/2013 | Smith | |
| 2013/0091815 A1 | 4/2013 | Smith | |
| 2015/0075301 A1 | 3/2015 | Scialo et al. | |

OTHER PUBLICATIONS

Search Report and Written Opinion, dated Jul. 21, 2015, corresponding to International Application No. PCT/US15/20129 (filed Mar. 12, 2015), related application, 11 pp.

* cited by examiner

FILTER AND BLOWER GEOMETRY FOR PARTICLE SAMPLER

CROSS-REFERENCE TO RELATED APPLICATIONS

This application claims the benefit of and priority to U.S. Provisional Application No. 61/953,101, filed on Mar. 14, 2014, which is hereby incorporated by reference in its entireties to the extent not inconsistent herewith.

STATEMENT REGARDING FEDERALLY SPONSORED RESEARCH OR DEVELOPMENT

Not applicable.

BACKGROUND OF INVENTION

The invention is in the field of particle sampling, collection and analysis. The invention relates generally to devices and methods for sampling and characterizing particles in fluids include air and process chemicals (e.g., gases and liquids) for applications including the evaluation of contaminants in a range of cleanroom and manufacturing environments.

Cleanrooms and clean zones are commonly used in semiconductor and pharmaceutical manufacturing facilities. For the semiconductor industry, an increase in airborne particulate concentration can result in a decrease in fabrication efficiency, as particles that settle on semiconductor wafers will impact or interfere with the small length scale manufacturing processes. For the pharmaceutical industry, where this type of real-time efficiency feedback is lacking, contamination by airborne particulates and biological contaminants puts pharmaceutical products at risk for failing to meet cleanliness level standards established by the Food and Drug Administration (FDA).

Standards for the classification of cleanroom particle levels and standards for testing and monitoring to ensuring compliance are provided by ISO 14664-1 and 14664-2. Aerosol optical particle counters are commonly used to determine the airborne particle contamination levels in cleanrooms and clean zones and liquid particle counters are used to optically measure particle contamination levels in process fluids. Where microbiological particles are a particular concern, such as in the pharmaceutical industry, not only is quantification of the number of airborne particles important, but evaluating the viability and identity of microbiological particles is also important. ISO 14698-1 and 14698-2 provide standards for evaluation of cleanroom and clean zone environments for biocontaminants.

Collection and analysis of airborne biological particles is commonly achieved using a variety of techniques including settling plates, contact plates, surface swabbing, fingertip sampling and impactor-based active air samplers. Cascade impactors have traditionally been used for collection and sizing of particles. In these devices, a series of accelerations and inertial impacts successively strip smaller and smaller particles from a fluid flow. Each single stage of an inertial impactor operates on the principle that particles suspended in air can be collected by forcing a dramatic change in the direction of the particle containing airflow, where the inertia of the particle will separate the particle from the airflow streamlines and allow it to impact on the surface. Biswas et al. describe the efficiency at which particles can be collected in a high velocity inertial impactor (*Environ. Sci. Technol.*, 1984, 18(8), 611-616).

In many cleanroom environments, retrieving size information from a particle impactor is not necessary. In this case, a single stage active air sampling impactor system is sufficient to collect biological particle concentrations subject to subsequent detection and analysis. In an impactor-based active air sampler used for collection of biological particles, the impact/collection surface commonly comprises a growth medium, such as an agar plate, as would be used with other biological particle collection techniques. After the particles are collected onto the growth media surface, the media is incubated to allow the biological particles to reproduce. Once the colonies reach a large enough size, they can be identified and characterized, for example using microscopic imaging, fluorescence, staining or other techniques, or simply counted visually by eye or by image analysis techniques.

For these types of biological particle collection and analysis techniques, various operational aspects are important to ensure efficient collection, detection and analysis. For example, the collection efficiency may be of high importance, as failing to detect that biological particles are present in cleanroom air can result in the cleanroom environment having higher levels of contamination than detected. Upon determination that under counting has occurred, pharmaceutical products made in those environments can be identified as failing to meet required standards, potentially leading to costly product recalls. Similarly, failing to ensure that the viability of collected biological particles is maintained during the collection process will also result in under counting. Such a situation can arise, for example, if the collected biological particles are destroyed, damaged or otherwise rendered non-viable upon impact with the growth medium, such that the collected particles do not replicate during the incubation process and, therefore, cannot be subsequently identified.

On the opposite extreme, biological particle concentrations can be overestimated due to false positives. Over counting of this nature arises where a biological particle that is not collected from the cleanroom air, but is otherwise placed in contact with the growth medium, is allowed to replicate during the incubation process and is improperly identified as originating from the cleanroom air. Situations that contribute to false positives include failing to properly sterilize the growth medium and collection system prior to particle collection and improper handling of the growth medium by cleanroom personnel as it is installed into a particle collection system and/or removed from the particle collection system and placed into the incubator. Again, this can result in a pharmaceutical product being identified as failing to meet required standards. Without sufficient measures to identify false positives, such a situation can result in pharmaceutical products that actually meet the required standards, but are destroyed due to an overestimation of biological particle concentration in the cleanroom air indicating that the standards were not met.

There remains a need in the art for particle collection systems capable of achieving efficient sampling of biological particles. For example, particle collection systems are need for cleanroom and manufacturing applications that provide high particle collection efficiencies while maintaining the viabilities of collected bioparticles. In addition, particle collection systems are need for cleanroom and manufacturing applications that reduce the occurrence of false positive detection events.

SUMMARY OF THE INVENTION

The invention generally provides devices and methods for sampling, detecting and/or characterizing particles. Devices and methods of the invention include particle samplers, impactors and counters, including a filter component for removing particles in the exhaust flow of the device, for example, to eliminate or minimize the potential for the device itself to provide source of particles in an environment undergoing particle monitoring. This aspect of the present devices and methods is particularly useful for monitoring particles in manufacturing environments requiring low levels of particles, such as cleanroom environments for electronics manufacturing and aseptic environments for manufacturing pharmaceutical and biological products, such as sterile medicinal products.

The invention provides, for example, a device having a fluid actuator component, such as a fan or pump, that generates a fluid flow from an environment undergoing monitoring through the device to allow collection and/or characterization (e.g., type of particle, size of particle, etc.) of particles in the flow and also including a filter component provide downstream of the fan or pump for removing particles from the fluid flow passing through the device. In some embodiments, for example, the filter component removes particles generated by the device (e.g., by the fluid actuator component) so as to produce an exhaust that is substantially free of particles of a preselected size criteria (e.g., cross sectional dimensions greater than or equal to a threshold value), thereby minimizing the potential impact of the device itself on the amount and types of particles present in the environment undergoing monitoring. Devices of some aspects provide a filter and fluid actuator geometry characterized by a compact overall form factor useful for a range of applications, including portable particle sampling and counting. In an embodiment, for example, the filter is provided in a housing that surrounds at least a portion of the motor of the fluid actuator so as to allow the filter and blower assembly to be more compact and easier to transport and handle than in conventional devices. Incorporation of a filter component surrounding, and in thermal contact with, at least portion of the motor of the fluid actuator also provides a significant benefit in that exhaust flow passing through the filter housing functions as a heat sink to cool the motor, thereby increasing the operational lifetime of the motor.

In an aspect, the invention provides a sampler comprising: (i) one or more fluid inlets for sampling a fluid flow; (ii) a particle analysis or collection region positioned in fluid communication with the one or more fluid inlets; (iii) a fan or pump positioned in fluid communication with the particle analysis or collection region, the fan or pump for generating the fluid flow through the system, wherein the fan or pump comprises a motor; and (iv) a filter in fluid communication with the fan or pump and positioned around at least a portion of the motor, the filter for filtering the fluid flow exhausted from the fan or pump. In an embodiment, for example, the device further comprises an air intake manifold for independently drawing air samples from one or more locations into the one or more fluid inlets. In some embodiments, the filter is arranged such that it removes particle from an exhaust flow from the device, for example, such that it removes at least a portion of particles generated by the fan or pump. In some embodiments, the filter is arranged such that the exhaust flow in contact with the filter is also provided in thermal contact with the motor, for example, wherein the filter is provided in a filter housing in thermal contact, and optionally physical contact, with the motor. In an embodiment, for example, the sampler comprises a fan, such as a fan comprising a plurality of rotatable fan blades for generating a fluid flow. In an embodiment, for example, the sampler comprises a pump such as reciprocating pump.

In an embodiment, for example, the device of this aspect comprises a portable air sampling device, including a portable particle impactor or particle counting device. In an embodiment, for example, the fluid flow is sampled from a clean room environment, such as a semiconductor manufacturing environment or an aseptic environment such as a pharmaceutical or biological manufacturing environment. In an embodiment, for example, the fluid flow is air or one or more process gases, such as process gases for a manufacturing application.

Devices and methods of the invention may implement a wide range of filter and fan and/or pump geometries including an enclosed or concentric geometry. In an embodiment, the filter has a central cavity and the motor is positioned in the central cavity. In an embodiment, for example, the filter has a toroid shape and the motor is positioned in a vacant central region of the toroid shape. In an embodiment, the filter has a cylindrical shape and the motor is positioned in a central aperture of the cylindrical shape, for example, wherein the fan or pump has a rotational axis and wherein the cylindrical shape has a cylindrical axis and wherein the rotational axis and the cylindrical axis are substantially parallel (e.g., within 10% of an absolutely parallel geometry) or optionally wherein the rotational axis and the cylindrical axis are coincident. In an embodiment, for example, the fluid flows through the one or more fluid inlets, through the particle analysis or collection region, into an intake of the fan or pump, to an exhaust of the fan or pump and through the filter, thereby filtering the fluid flow.

Systems of the invention may implement a range of fluid actuators including fans and pump. Use of a fluid actuator comprising a fan is preferred in some embodiments given its compatible with a range of useful overall device geometries and fluid flow rates. A range of fan types, geometries and flow rates are useful in the present devices and methods. In an embodiment, for example, the fan comprises a centrifugal blower, regenerative blower or radial blower. In an embodiment, for example, the fan comprises an axial fan, a high static pressure fan or a counter-rotating fan. In an embodiment, for example, the motor is positioned to rotate the fan blades around a rotational axis. Example fans useful in some embodiments of the invention include a BLDC Low-voltage blower from Ametek®, a G-BH10 blower from Elmo Rietschle, a Minispiral™ HDC variable flow regenerative blower from Ametek® and a C55H1 radial blower from MUS international. In an embodiment, the fluid actuator component of the present methods and systems is a pump, such as a reciprocating pump.

In an embodiment, for example, the fan or pump is for providing a flow rate through the system selected from the range of 0.05 CFM to 10 CFM. In an embodiment, for example, the fan or pump is rated for generating a pressure of 1 to 100 inches of water. The invention also includes device comprising a plurality of fans and/or pumps, for example, wherein the plurality of fans and/or pumps are arranged in a parallel flow configuration or a serial flow configuration. In an embodiment, for example, the filter is provided in a filter housing provided in thermal contact with certain other components of the device, such as the motor, wherein passage of the fluid flow exhausted from the fan or pump through the filter housing cools the motor.

A range of filter types and geometries are useful in the present devices and methods. In an embodiment, for example, the filter removes at least 90% of particles having cross sectional dimensions greater than or equal to 0.5 µm, optionally for some applications at least 99% of particles having cross sectional dimensions greater than or equal to 0.5 µm, optionally for some applications at least 99.9% of particles having cross sectional dimensions greater than or equal to 0.5 µm and optionally for some applications at least 99.97% of particles having cross sectional dimensions greater than or equal to 0.3 µm. In an embodiment, the filter is a HEPA filter. In an embodiment, for example, the filter has an inner cross-sectional dimension selected from the range of 1 to 4 inches and an outer cross-sectional dimension selected from the range of 2 to 10 inches. In an embodiment, for example, the device further comprises a filter housing positioned around the filter, the filter housing comprising an housing inlet in fluid communication with the fan or pump and a housing outlet in fluid communication with the housing inlet, optionally wherein the fluid flow flows from the housing inlet through the filter to the housing outlet, thereby filtering the fluid flow. In an embodiment, the device of the present invention comprises a plurality of filters, optionally provided in series and/or parallel configuration.

Devices of the invention include impactors for sampling particles, including biological particles such as microorganisms. In an embodiment, for example, the device comprises one or more fluid inlets comprising one or more air intake apertures and wherein the particle analysis or collection region comprises an impact plate positioned in fluid communication with the one or more air intake apertures for collecting particles from the fluid flow. In an embodiment, the air intake apertures comprise air intake slits and/or holes, for example, provided in a preselected pattern. Alternatively, the samplers of the invention may comprise a single air intake aperture. In an embodiment, for example, the device of the invention comprises an active air impactor sampler or a slit-to-agar sampler. In an embodiment, for example, the impact plate is positioned adjacent to the one or more air intake apertures in the particle analysis or collection region for collecting impacted particles from the fluid flow. In an embodiment, for example, the impact plate comprises a petri dish for culturing impacted biological particles from the fluid flow. In an embodiment, for example, the petri dish is analyzed to determine a number of impacted biological particles from the fluid flow. In an embodiment, for example, the petri dish is removable. In an embodiment, for example, the impact plate comprises a growth medium specific to one or more classes of biological organisms. In an embodiment, for example, the impact plate comprises a rotatable impact plate. In an embodiment, for example, the device of the invention comprises a slit-to-agar microbial sampler.

Devices and methods of the invention, including sampling devices, such as impactors, are useful for a wide range of types and rates of fluid flows such as air flows. In an embodiment, for example, a linear flow velocity of the fluid flow through the one or more air intake apertures is 5 to 50 meter/sec. In an embodiment, for example, the fluid flow through the one or more air intake apertures is a substantially laminar flow or a laminar flow.

In an embodiment, the device comprises a plurality of air intake apertures, for example, wherein the plurality of air intake apertures are arranged radially around a central point. In an embodiment, for example, the plurality of air intake apertures allow for distinguishing whether particles present on the impact plate are impacted particles from the fluid flow or are not from the fluid flow. In an embodiment, for example, each of the one or more air intake apertures corresponds to an impact area on the impact plate. In an embodiment, for example, the impact areas for each of the one or more air intake apertures together comprise less than 10% of a surface area of the impact plate. In an embodiment, for example, the one or more air intake apertures comprise air intake slits and each of the air intake slits has a length selected the range of 1.0 cm to 10 cm and a width selected from the range of 0.05 cm to 1.0 cm. In an embodiment, for example, a flow direction of the fluid flow changes by 80° or more after as fluid flow passes through the one or more air intake apertures and past the impact plate, wherein particles present in the fluid flow are impacted onto the impact plate. In an embodiment, for example, the one or more air intake apertures are located on a removable impactor sampling head.

Devices of the present invention also include particle counting devices, such as optical particle counters. In an embodiment, for example, the particle analysis or collection region comprises: (i) a source of electromagnetic radiation positioned to direct electromagnetic radiation through the fluid flow from the one or more fluid inlets, wherein electromagnetic from the source interacts with particles present in the fluid flow to generate scattered or emitted electromagnetic radiation; (ii) an optical collection system positioned in optical communication with the fluid flow, the optical collection system for collecting at least a portion of the scattered or emitted electromagnetic radiation; and (iii) a detector positioned in optical communication with the optical collection system, the detector for detecting a collected portion of the scattered or emitted electromagnetic radiation and for producing a signal characteristic of the particles present in the fluid flow. In an embodiment, for example, the source of electromagnetic radiation comprises a laser. In an embodiment, for example, the signal characteristic of the particles comprises one or more of a size of the particles, a size distribution of the particles and/or a number of the particles.

In another aspect, the invention provides methods of sampling, detecting or characterizing particles. In an embodiment, for example, a method of evaluating particles in an environment comprises steps of: (i) sampling a fluid flow from the environment by passing the fluid flow through one or more fluid inlets; (ii) passing the fluid flow through a particle analysis or collection region; (iii) flowing the fluid flow using a fan or pump comprising a motor through a filter, wherein the filter is positioned at least partially around the motor, thereby filtering the fluid flow; and (iv) analyzing particles present in the fluid flow in the particle analysis or collection region or collecting particles in the fluid flow in the particle analysis or collection region for subsequent analysis, thereby evaluating particles in the environment. Methods of the invention include methods of collecting and/or characterizing biological particles, such as microorganisms. Methods of the invention include methods of counting or determining the size of particles, such as optical particle counting methods. In an embodiment, for example, the method utilizes a fan, such as a fan comprising a plurality of rotatable fan blades for generating a fluid flow. In an embodiment, for example, the method utilizes a pump such as reciprocating pump.

Methods of this aspect can use any of the devices, including samplers, impactors and particle counters, described herein. In an embodiment, for example, a method of the invention further comprises engaging the motor to rotate the fan blades or pump, thereby flowing the fluid flow from the environment through the one or more fluid inlets to the particle analysis or collection region; and analyzing particles present in the fluid flow in the particle analysis or collection region or collecting particles present in the fluid flow in the particle analysis or collection region for subsequent analysis, thereby evaluating the particles in the environment.

In another aspect, the invention provides a sampler comprising: (i) one or more fluid inlets for sampling a fluid flow from an environment undergoing monitoring; (ii) a particle analysis or collection region positioned in fluid communication with the one or more fluid inlets; (iii) a fluid actuator positioned in fluid communication with the particle analysis or collection region, the fluid actuator for generating the fluid flow; and (iv) an exhaust system for controlling an exhaust flow generating by the fluid actuator so as to direct the exhaust flow into a release environment separate from the environment undergoing monitoring. In another aspect, the invention provides a method of sampling particles in an environment undergoing monitoring, the method comprising steps of: (i) sampling a fluid flow from the environment undergoing monitoring by passing the fluid flow through one or more fluid inlets; (ii) passing the fluid flow through a particle analysis or collection region, thereby generating an exhaust flow from the particle analysis or collection region; and (iii) releasing the exhaust flow into a release environment separate from the environment undergoing monitoring. In an embodiment, for example, the fluid actuator is a fan or a pump. In an embodiment, for example, the exhaust flow passes through an exhaust port and tubing away from the environment undergoing monitoring. In an embodiment, for example, the exhaust flow is released into a recovery system or recovery region.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 1A provides a schematic diagram illustrating the general construction of a particle impactor and FIG. 1B illustrates an expanded view of a particle impactor to further illustrate the operational principal.

FIG. 2 provide a schematic diagram of a portable impactor of the invention for sampling biological particles.

FIGS. 3A and 3B provide schematic diagrams providing a perspective side view and a cross sectional view, respectively, of the filter and blower components of the impactor show in FIG. 2.

FIGS. 4A, 4B and 4C provide schematic diagrams depicting a particle sampling device of the invention having a fluid exhaust system for avoiding release of exhaust into the environment undergoing monitoring. FIG. 4A provides a perspective view of a particle sampling device showing a removable exhaust grill component. FIG. 4B provides an exploded view of a particle sampling device showing an exhaust port component. FIG. 4C provides a front view of a particle sampling device showing an exhaust port component.

DETAILED DESCRIPTION OF THE INVENTION

In general, the terms and phrases used herein have their art-recognized meaning, which can be found by reference to standard texts, journal references and contexts known to those skilled in the art. The following definitions are provided to clarify their specific use in the context of the invention.

"Particle" refers to a small object which is often regarded as a contaminant. A particle can be any material created by the act of friction, for example when two surfaces come into mechanical contact and there is mechanical movement. Particles can be composed of aggregates of material, such as dust, dirt, smoke, ash, water, soot, metal, minerals, or any combination of these or other materials or contaminants. "Particles" may also refer to biological particles, for example, viruses, spores and microorganisms including bacteria, fungi, archaea, protists, other single cell microorganisms and specifically those microorganisms having a size on the order of 1-20 μm. Biological particles include viable biological particles capable of reproduction, for example, upon incubation within a growth media. A particle may refer to any small object which absorbs or scatters light and is thus detectable by an optical particle counter. As used herein, "particle" is intended to be exclusive of the individual atoms or molecules of a carrier fluid, for example, such gases present in air (e.g., oxygen molecules, nitrogen molecules, argon molecule, etc.) or process gases. Some embodiments of the present invention are capable of sampling, collecting, detecting, sizing, and/or counting particles comprising aggregates of material having a size greater than 50 nm, 100 nm, 1 μm or greater, or 10 μm or greater. Specific particles include particles having a size selected from 50 nm to 50 μm, a size selected from 100 nm to 10 μm, or a size selected from 500 nm to 5 μm.

The expression "sampling a particle" broadly refers to collection of particles in a fluid flow, for example, from an environment undergoing monitoring. Sampling in this context includes transfer of particles in a fluid flow to an impact surface, for example, the receiving surface of a growth medium. Alternatively sampling may refer to passing particles in a fluid through a particle analysis or collection region, for example, for optical detection and/or characterization. Sampling may refer to collection of particles having one or more preselected characteristics, such as size (e.g., cross sectional dimension such as diameter, effective diameter, etc.), particle type (biological or nonbiological, viable or nonviable, etc.) or particle composition. Sampling may optionally include analysis of collected particles, for example, via subsequent optical analysis, imaging analysis or visual analysis. Sampling may optionally include growth of viable biological particles, for sample, via an incubation process involving a growth medium. A sampler refers to a device for sampling particles.

Impactor refers to a device for sampling particles. In some embodiments, an impactor comprises a sample head including one or more intake apertures for sampling a fluid flow containing particles, whereby at least a portion of the particles are directed on to an impact surface for collection, such as the receiving surface of a growth medium (e.g., culture medium such as agar, broth, etc.) or a substrate such as a filter. Impactors of some embodiment, provide a change of direction of the flow after passage through the intake apertures, wherein particles having preselected characteristics (e.g., size greater than a threshold value) do not make the change in direction and, thus, are received by the impact surface.

The expression "detecting a particle" broadly refers to sensing, identifying the presence of and/or characterizing a particle. In some embodiments, detecting a particle refers to counting particles. In some embodiments, detecting a particle refers to characterizing and/or measuring a physical characteristic of a particle, such as diameter, cross sectional dimension, shape, size, aerodynamic size, or any combination of these. A particle counter is a device for counting the number of particles in a fluid or volume of fluid, and optionally may also provide for characterization of the particles, for example, on the basis of size (e.g., cross sectional dimension such as diameter or effective diameter), particle type (e.g. biological or nonbiological, or particle composition. An optical particle counter is a device that detects particles by measuring scattering, emission or absorbance of light by particles.

"Flow direction" refers to an axis parallel to the direction the bulk of a fluid is moving when a fluid is flowing. For fluid flowing through a straight flow cell, the flow direction is parallel to the path the bulk of the fluid takes. For fluid flowing through a curved flow cell, the flow direction may be considered tangential to the path the bulk of the fluid takes.

"Optical communication" refers to an orientation of components such that the components are arranged in a manner that allows light or electromagnetic radiation to transfer between the components.

"Fluid communication" refers to the arrangement of two or more objects such that a fluid can be transported to, past, through or from one object to another. For example, in some embodiments two objects are in fluid communication with one another if a fluid flow path is provided directly between the two objects. In some embodiments, two objects are in fluid communication with one another if a fluid flow path is provided indirectly between the two objects, such as by including one or more other objects or flow paths between the two objects. For example, in one embodiment, the following components of a particle impactor are in fluid communication with one another: one or more intake apertures, an impact surface, a fluid outlet, a flow restriction, one or more a pressure sensors, and/or a flow generating device. In one embodiment, two objects present in a body of fluid are not necessarily in fluid communication with one another unless fluid from the first object is drawn to, past and/or through the second object, such as along a flow path.

"Flow rate" refers to an amount of fluid flowing past a specified point or through a specified area, such as through intake apertures or a fluid outlet of a particle impactor. In one embodiment a flow rate refers to a mass flow rate, i.e., a mass of the fluid flowing past a specified point or through a specified area. In one embodiment a flow rate is a volumetric flow rate, i.e., a volume of the fluid flowing past a specified point or through a specified area.

"Pressure" refers to a measure of a force exhibited per unit area. In an embodiment, a pressure refers to a force exhibited by a gas or fluid per unit area. An "absolute pressure" refers to a measure of the pressure exerted by a gas or fluid per unit area as referenced against a perfect vacuum, near vacuum, a calibration pressure and/or volume exerting zero force per unit area. Absolute pressure is distinguished from a "differential pressure" or "gauge pressure", which refers to a relative or difference in force exhibited per unit area in excess of or relative to a second pressure, such as an upstream pressure, a downstream pressure, an ambient pressure or atmospheric pressure.

Figure 1B:
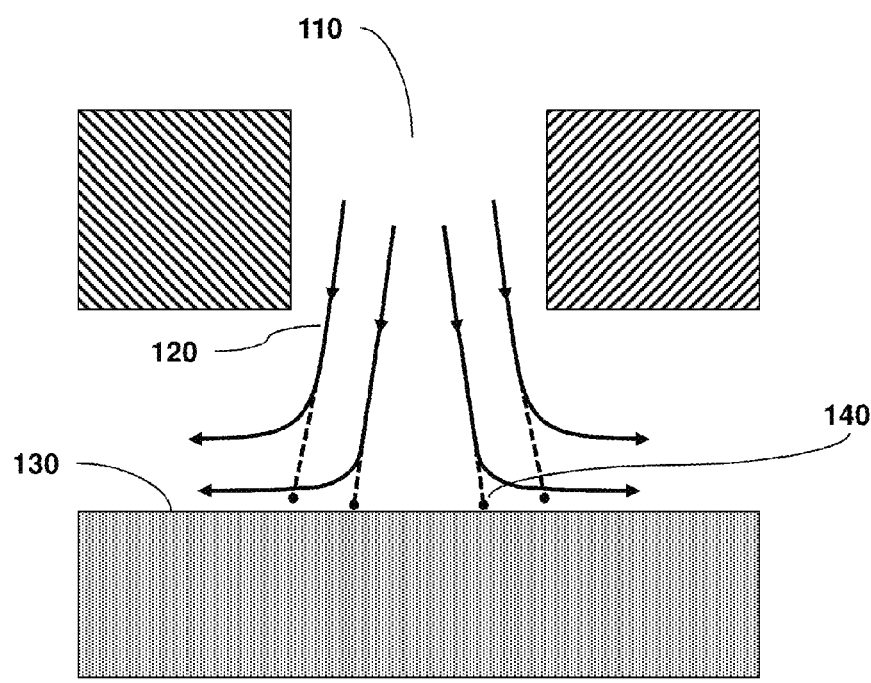

FIG. 1A provides a schematic diagram illustrating the general construction of a particle impactor and FIG. 1B illustrates an expanded view of a particle impactor to further illustrate the operational principal. As shown in these Figures, gas flow is directed through an intake aperture 110 in a sampling head 100 where it is accelerated towards an impact surface 130, which forces the gas to rapidly change direction, following flow paths 120. Due to their momentum, particles 140 entrained in the gas flow are unable to make the rapid change in direction and impact on the impact surface 130. In the embodiment shown in FIGS. 1A and 1B, impact surface 130 is supported by impactor base 150. In embodiments, impact surface 130 comprises the receiving surface of a growth medium, such as agar, provided in a growth medium container or petri dish. Viable biological particles collected on the impact surface, for example, can subsequently be grown and evaluated to provide an analysis of the composition of the fluid flow sampled. For collection of biological particles on the impact surface, control over the distance between the exit of the intake aperture and the impact surface is important. If the distance is too large, for example, the particles may sufficiently follow the fluid path so as to avoid impact with the impact surface. If the distance is too small, however, the particles may impact the impact surface with a force sufficient to render the particles nonviable and, thereby unable to reproduce.

Portable devices like a biological sampler or portable particle counter benefit from a compact form factor for easy transport, handling and operation. These devices also benefit from the use of a blower to generate fluid flow and a filter provided downstream to remove particles from gas flow exhausted from the device to avoid introduction of particles generated from the device into the environment undergoing monitoring. Incorporation of a traditional filter may require placement beside the blower, thereby resulting in a large and bulky device, for example, less suitable for portable use. In aspect of the invention, wrapping the filter around the blower creates a more compact and user friendly device.

Figure 2:
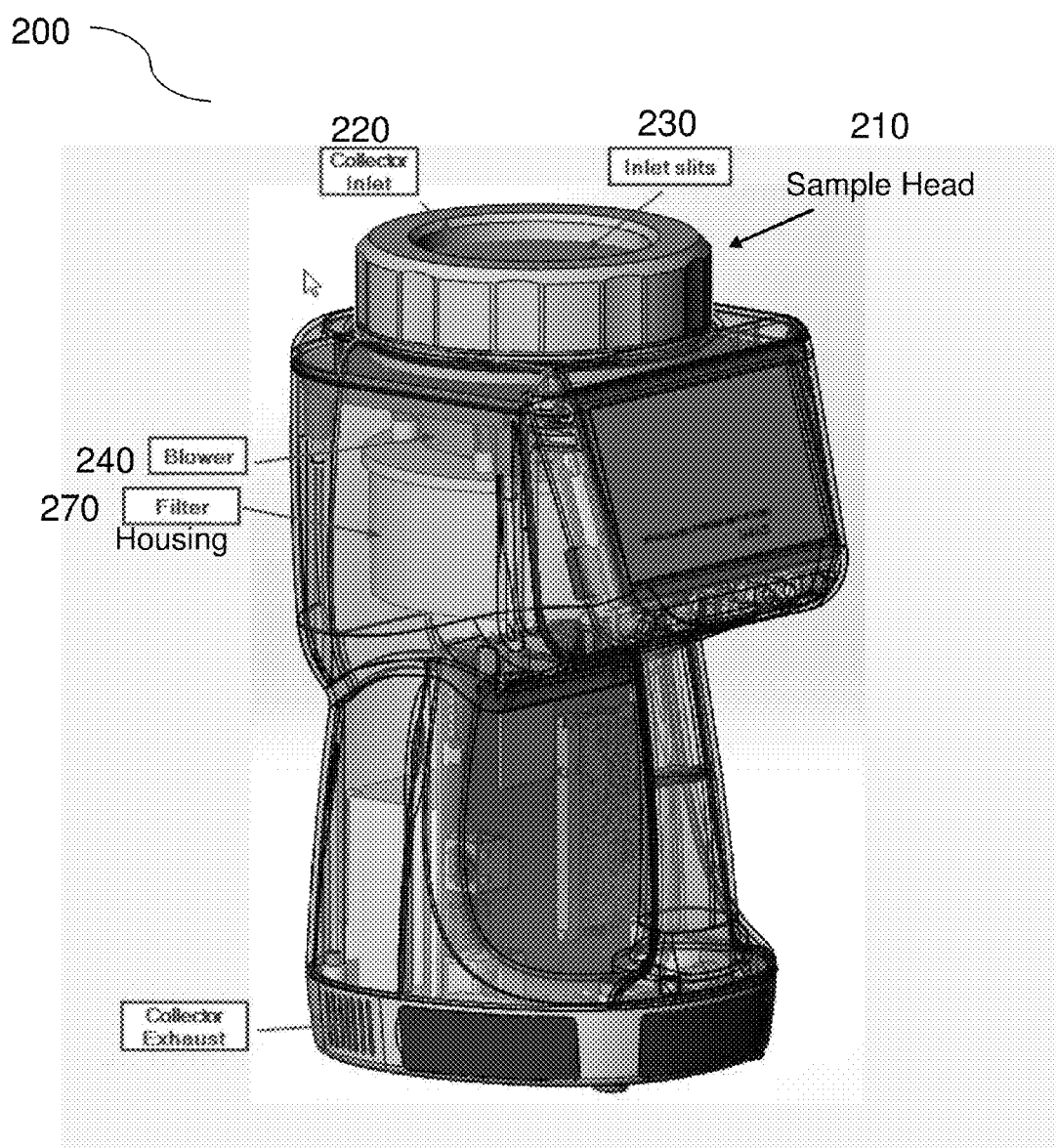

FIG. 2 provide a schematic diagram of a portable impactor system of the invention for sampling biological particles. As shown in FIG. 2, the impactor system (200) comprises a sample head (210) having a collector inlet (220) with a plurality of inlet slits (230) in fluid communication with an impactor surface and an outlet. In some embodiments, for example, the impact surface is the receiving surface of a growth medium, such as an agar plate, for collection and subsequent growth of biological particles in the sampled flow. A blower (240) is operationally connected with the outlet of the impactor base so as to be able to generate a flow of gas from an environment undergoing monitoring through the sample head (210) and impactor base. Exhaust from the blower is passed through a filter housing (260) containing filter media (270) to remove particles in the fluid flow, including any particles generated by the blower, and subsequently released to the environment undergoing monitoring.

Figure 3A:
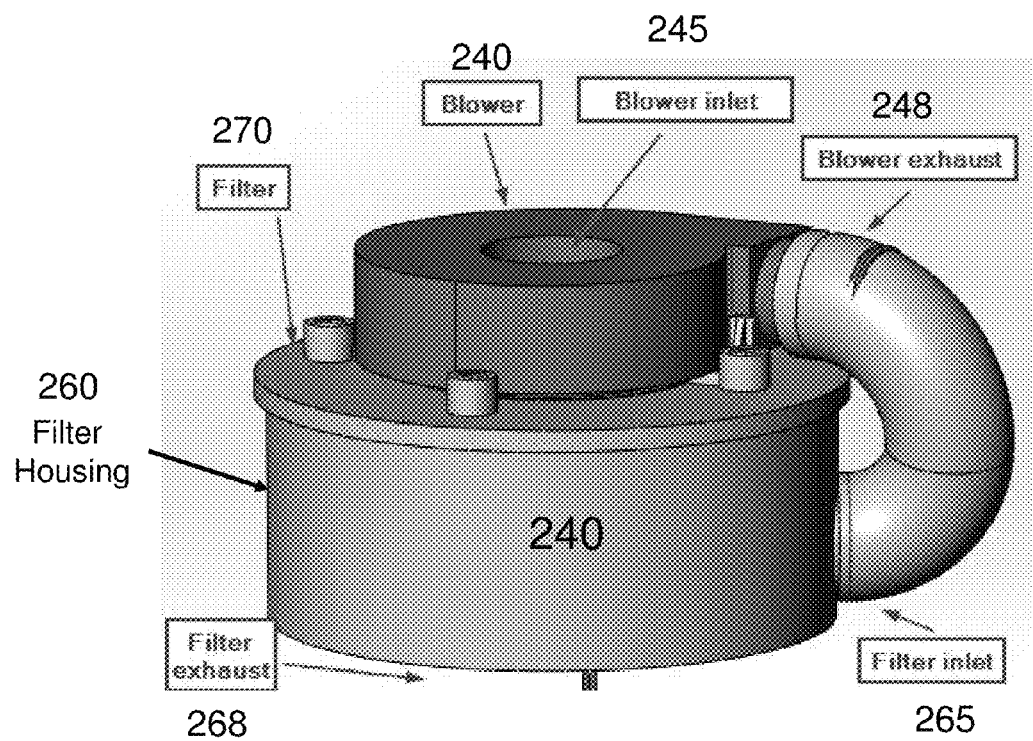
Figure 3B:
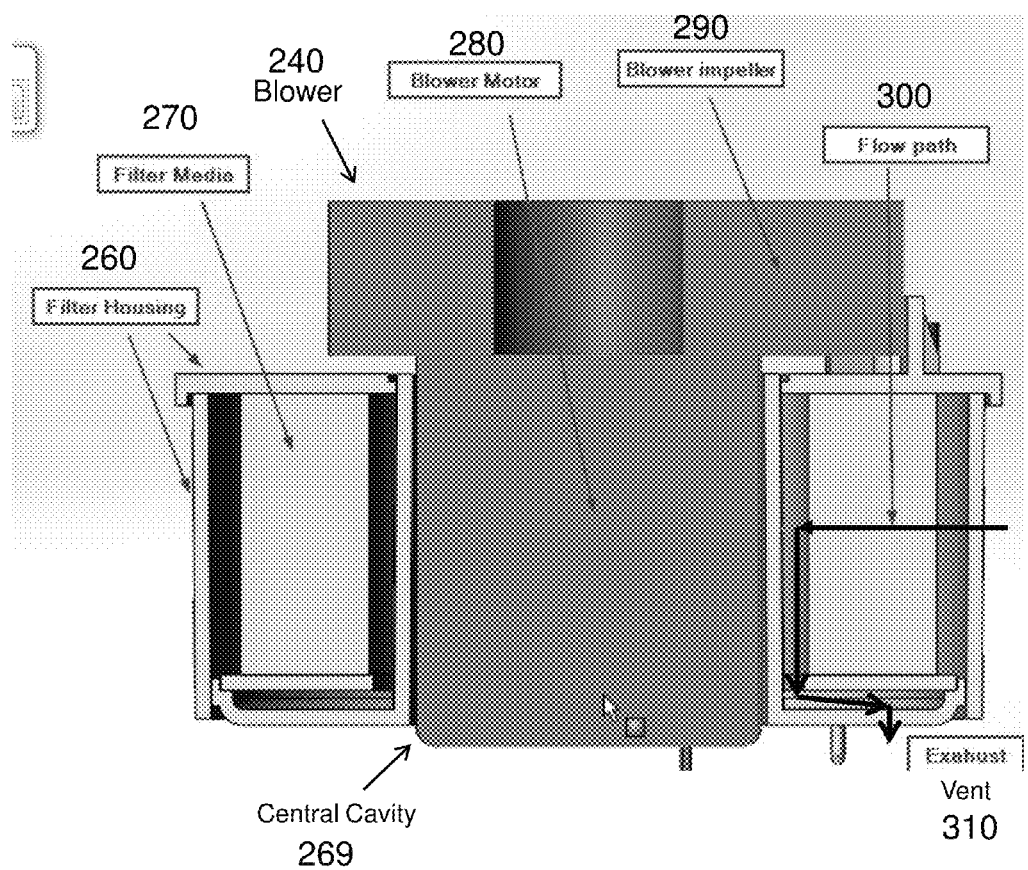

FIGS. 3A and 3B provide schematic diagrams providing a perspective side view and a cross sectional view, respectively, of the filter and blower components of the impactor show in FIG. 2. As shown in these Figures, the filter housing (260) and blower (240) are provided in a concentric geometry, wherein the cylindrical filter housing (260) has a central cavity (269) for accommodating at least a portion of the blower (240), such as the motor (280) of the blower. As illustrated in these Figures, the cylindrical filter (270) is made hollow in the center so that a blower motor (280) can be inserted into it to provide a compact form factor suitable for portable use. Optionally, the filter housing (260) is provided in thermal contact, and optionally in physical contact for some applications, with at least a portion of the blower (240), such the blower motor (280). Also shown in FIGS. 3A and 3B is blower impeller (290), blower inlet (245), blower exhaust (248), filter inlet (265) and filter exhaust (268). The resultant combined blower and filter assembly is more compact than two separate components. In addition, the concentric geometry of the illustrated filter and blower configuration provide for efficient thermal transport from the motor to the fluid passing through the filter housing, thereby resulting in cooling of the motor which may result in more stable and longer operation of the system.

Also shown in FIG. 3B is the flow path (300, schematically represented by arrows) of exhaust from the blower through the filter housing containing filter media and out an outlet (e.g., exhaust vent) of the device. As shown in this Figure, exhaust from the blower is passed through the blower exhaust line and into an inlet in the filter housing. Within the filter housing, the exhaust contacts filter media, such as a HEPA filter, wherein particles are removed. After interaction with the filter, the exhaust is subsequently passed through an outlet of the filter housing and is released into the environment undergoing monitoring. In this flow configuration, the filter component minimizes the amount of particles released into the environment from the impactor, thereby maintaining the cleanliness of the environment.

The invention also provides devices and methods for sampling, collecting and analyzing particles including an exhaust system wherein exhaust from a particle sampler or particle counter is diverted away from the environment undergoing monitoring, for example, to avoid disruption of the flow conditions and/or composition of the environment undergoing monitoring. This aspect of the invention has the benefit of maintaining the flow conditions and/or cleanliness of the environment undergoing monitoring, such as a manufacturing environment (e.g., cleanroom or aseptic environment) requiring a specific composition or flow configuration for a given process.

In an embodiment, for example, devices of the invention incorporate an exhaust connection to allow the exhaust flow (e.g., air or one or more process gases) from the instrument to be moved away from the instrument and the measurement area, thereby avoiding a disruption to the composition or flow of air of the rest of the monitoring location. In an embodiment, for example, the operation the instrument exhausts the air that is brought into the device for analysis or collection via an exhaust port. This port may optionally direct or disrupt the air flow out of the instrument through the use of vents, holes or louvers. The reason for this direction or disruption of the air is to minimize the impact this air flow has on the laminar air flow of the room. The air may be exhausted horizontal to the vertical air flow of the room (or any other direction).

Figure 4A:
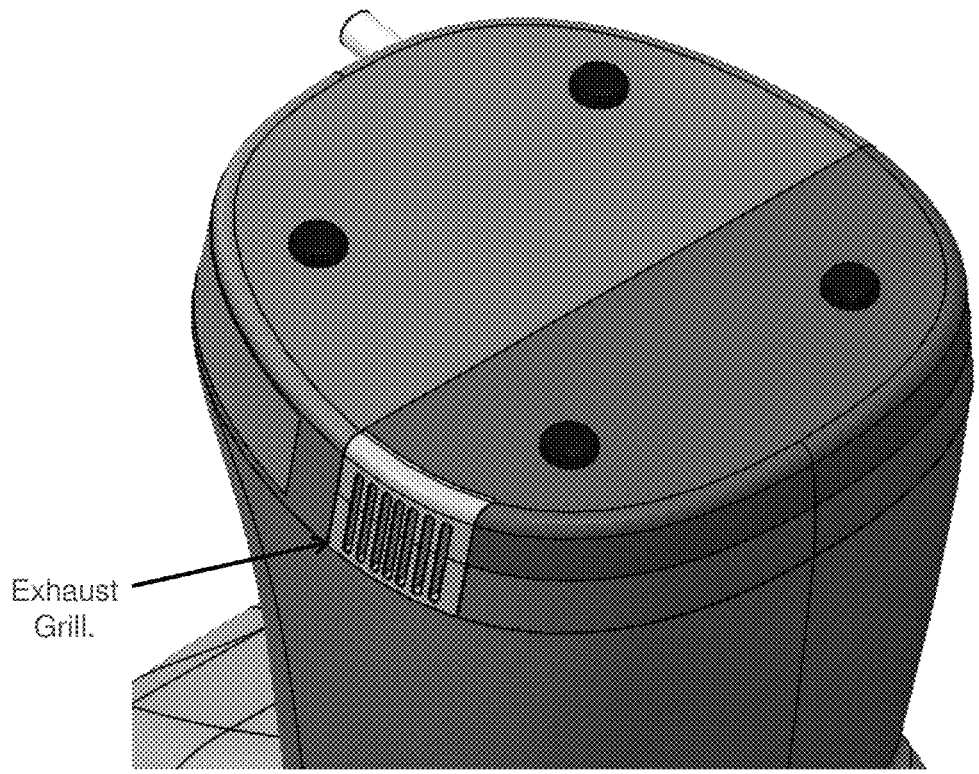
Figure 4B:
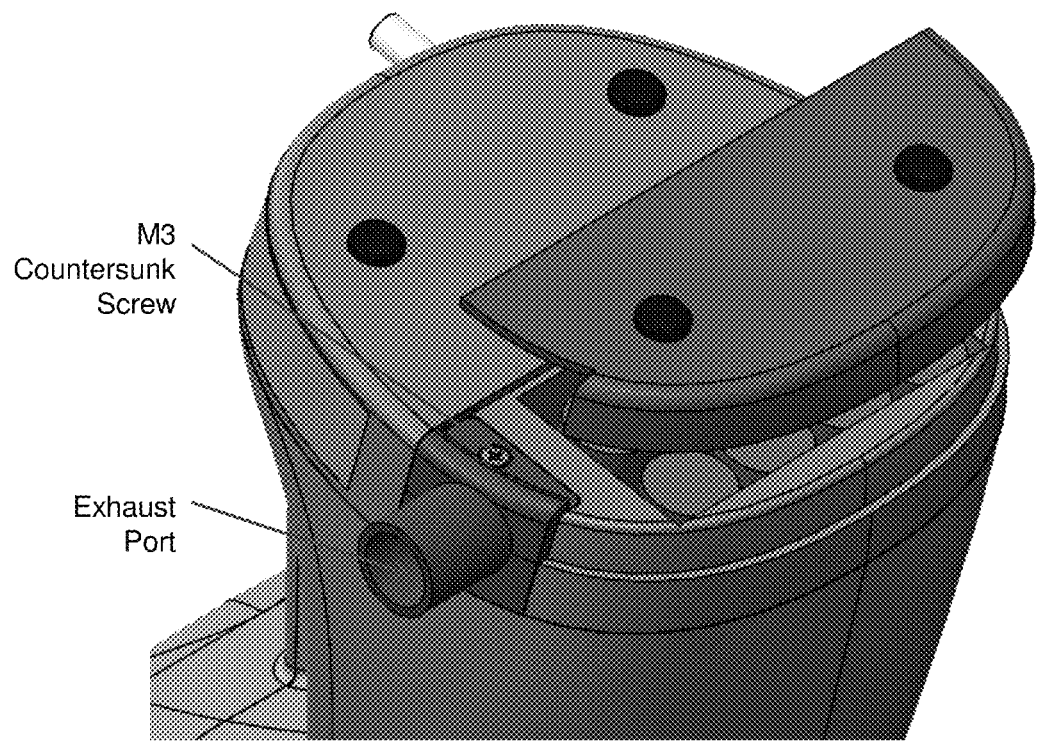
Figure 4C:
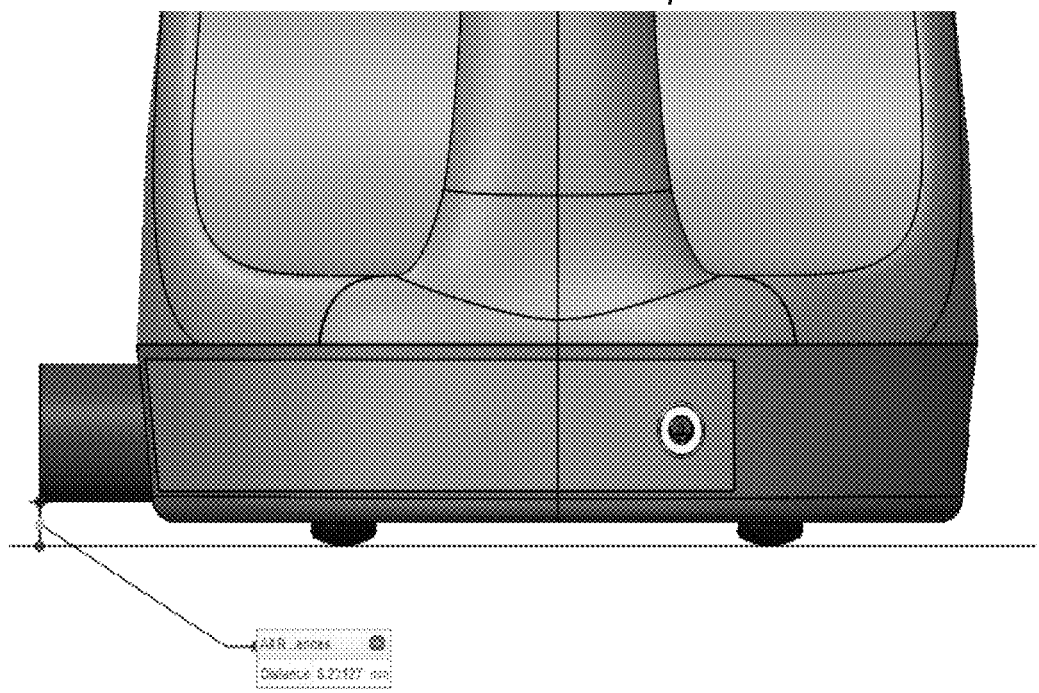

FIGS. 4A, 4B and 4C provide schematic diagrams depicting a particle sampling device of the invention having a fluid exhaust system for controlling release of exhaust into the environment undergoing monitoring. FIG. 4A provides a perspective view of a particle sampling device showing a removable exhaust grill component. FIG. 4B provides an exploded view of a particle sampling device showing an exhaust port component. FIG. 4C provides a front view of a particle sampling device showing an exhaust port component. As will be understood by one having skill in the art, the exhaust port component may be adapted to accommodate tubing for passage of exhaust to a location other than the environment undergoing monitoring, such as a designated recovery system or region.

To eliminate or minimize disruption to the room's air flow the device has the ability to connect tubing directly to the instrument allow the air flow to be directed away from the location where it was sampled and exhausted in a less critical location. This location may just be a few feet away or into an air recovery system. This also allows the air being exhausted from the instrument to not be recirculated onto the customer finished product eliminating or reducing risk of contamination to the area. This connection of tubing is facilitated by replacing the exhaust port with a tubing connection on the device and by using a fitting that can have an adapter screwed into it for the device.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim 1n the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Every embodiment or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A sampler comprising:
    one or more fluid inlets for sampling a fluid flow;
    a particle analysis or collection region positioned in fluid communication with said one or more fluid inlets;
    a fan or pump positioned in fluid communication with said particle analysis or collection region, said fan or pump for generating said fluid flow, wherein said fan or pump comprises a motor; and
    a filter in fluid communication with said fan or pump and positioned around at least a portion of said motor, said filter for filtering said fluid flow exhausted from said fan or pump, wherein said filter has a toroid shape or cylindrical shape and said motor is positioned in a central region of said toroid shape or cylindrical shape.

2. The sampler of claim 1, wherein said fan has a rotational axis and said filter has a cylindrical shape, wherein said cylindrical shape has a cylindrical axis and said rotational axis and said cylindrical axis are parallel.

3. The sampler of claim 1, wherein said fluid flows through said one or more fluid inlets, through said particle analysis or collection region, into an intake of said fan or pump, to an exhaust of said fan or pump and through said filter, thereby filtering said fluid flow.

4. The sampler of claim 1, further comprising an air intake manifold for independently drawing air samples from one or more locations into said one or more fluid inlets.

5. The sampler of claim 1, wherein said filter removes at least 90% of particles having cross sectional dimensions greater than or equal to 0.5 μm.

6. The sampler of claim 1, wherein said fan is a centrifugal blower, regenerative blower, radial blower, axial fan, high static pressure fan, or counter-rotating fan.

7. The sampler of claim 1, wherein said pump is a reciprocating pump.

8. The sampler of claim 1, wherein said fan or pump provides a flow rate selected from the range of 0.05 CFM to 10 CFM.

9. The sampler of claim 1, wherein said filter is provided in a filter housing provided in thermal contact with said motor, wherein passage of said fluid flow exhausted from said fan or pump through said filter housing cools said motor.

10. The sampler of claim 1, further comprising a filter housing positioned around said filter, said filter housing comprising a housing inlet in fluid communication with said fan or pump and a housing outlet in fluid communication with said housing inlet.

11. The sampler of claim 10, wherein said fluid flow flows from said housing inlet through said filter to said housing outlet, thereby filtering said fluid flow.

12. The sampler of claim 1, wherein said one or more fluid inlets comprise one or more air intake apertures and wherein said particle analysis or collection region comprises an impact plate positioned in fluid communication with said one or more air intake apertures for collecting particles from said fluid flow.

13. The sampler of claim 12, comprising an active air impactor sampler or a slit-to-agar sampler.

14. The sampler of claim 12, wherein said impact plate is positioned adjacent to said one or more air intake apertures in said particle analysis or collection region for collecting impacted particles from said fluid flow.

15. The sampler of claim 12, wherein said impact plate comprises a petri dish for culturing impacted biological particles from said fluid flow.

16. The sampler of claim 15, wherein said petri dish is removable or is integral to an impactor base.

17. The sampler of claim 12, wherein said impact plate comprises a growth medium specific to one or more classes of biological organisms.

18. The sampler of claim 12, wherein said impact plate comprises a rotatable impact plate.

19. The sampler of claim 12, wherein a linear flow velocity of said fluid flow through said one or more air intake apertures is 5 to 50 meter/sec.

20. The sampler of claim 12, wherein said fluid flow through said one or more air intake apertures is laminar.

21. The sampler of claim 12, further comprising a plurality of air intake apertures, wherein said plurality of air intake apertures are arranged radially around a central point.

22. The sampler of claim 12, further comprising a plurality of air intake apertures, wherein said plurality of air intake apertures allow for distinguishing whether particles present on said impact plate are impacted particles from said fluid flow or are not from said fluid flow.

23. The sampler of claim 12, wherein each of said one or more air intake apertures corresponds to an impact area on said impact plate.

24. The sampler of claim 12, wherein a flow direction of said fluid flow changes by 80° or more after as fluid flow passes through said one or more air intake apertures and past said impact plate, wherein particles present in said fluid flow are impacted onto said impact plate.

25. The sampler of claim 12, wherein said one or more air intake apertures are located on a removable impactor sampling head.

26. The sampler of claim 1, wherein said particle analysis or collection region comprises:
- a source of electromagnetic radiation positioned to direct electromagnetic radiation through said fluid flow from said one or more fluid inlets, wherein electromagnetic from said source interacts with particles present in said fluid flow to generate scattered or emitted electromagnetic radiation;
- an optical collection system positioned in optical communication with said fluid flow, said optical collection system for collecting at least a portion of said scattered or emitted electromagnetic radiation; and
- a detector positioned in optical communication with said optical collection system, said detector for detecting a collected portion of said scattered or emitted electromagnetic radiation and for producing a signal characteristic of said particles present in said fluid flow.

* * * * *